United States Patent [19]

Telorack

[11] Patent Number: 4,691,335
[45] Date of Patent: Sep. 1, 1987

[54] PRIMARY RADIATION DIAPHRAGM FOR X-RAY DIAGNOSTICS DEVICES

[75] Inventor: Gerhard Telorack, Aurachtal, Fed. Rep. of Germany

[73] Assignee: Siemens Aktiengesellschaft, Berlin and Munich, Fed. Rep. of Germany

[21] Appl. No.: 795,245

[22] Filed: Nov. 5, 1985

[30] Foreign Application Priority Data

Dec. 11, 1984 [DE] Fed. Rep. of Germany ... 8436281[U]

[51] Int. Cl.$^4$ .............................................. G21K 1/04
[52] U.S. Cl. .................................... 378/152; 378/150
[58] Field of Search ................ 378/147, 150, 151, 152

[56] References Cited

U.S. PATENT DOCUMENTS

| | | | |
|---|---|---|---|
| 1,909,118 | 5/1933 | Raab | 378/152 |
| 4,203,037 | 5/1980 | Gur et al. | |
| 4,315,146 | 2/1982 | Rudin | |
| 4,380,819 | 4/1983 | Everett et al. | 378/175 |
| 4,577,341 | 3/1986 | Schwieker et al. | 378/152 |

FOREIGN PATENT DOCUMENTS 0068202  5/1983  European Pat. Off.
1441312 10/1968  Fed. Rep. of Germany.
2842659 10/1980  Fed. Rep. of Germany.
3236082  3/1984  Fed. Rep. of Germany.
1258028  5/1971  United Kingdom.

Primary Examiner—Carolyn E. Fields
Assistant Examiner—Joseph A. Hynds
Attorney, Agent, or Firm—Hill, Van Santen, Steadman & Simpson

[57] ABSTRACT

A primary X-ray diaphragm for X-ray diagnostics devices has at least two pairs of diaphragm plates, each pair being in a common plane and the pairs being in spaced parallel planes, and a common drive connection to both pairs of diaphragm plates for simultaneously moving the plates in each pair in opposite directions perpendicular to a central X-ray beam, the drive connection moving the plates in the plane which is closer to the X-ray focus at a faster rate than the plates in the plane farther from the focus so that the plates in the spaced planes overlap at every plate position. The drive connection may be in the form of pulleys of different diameters connected to a common axle, with tooth belts being entrained around the pulleys and respectively connected to the pairs of plates.

2 Claims, 2 Drawing Figures

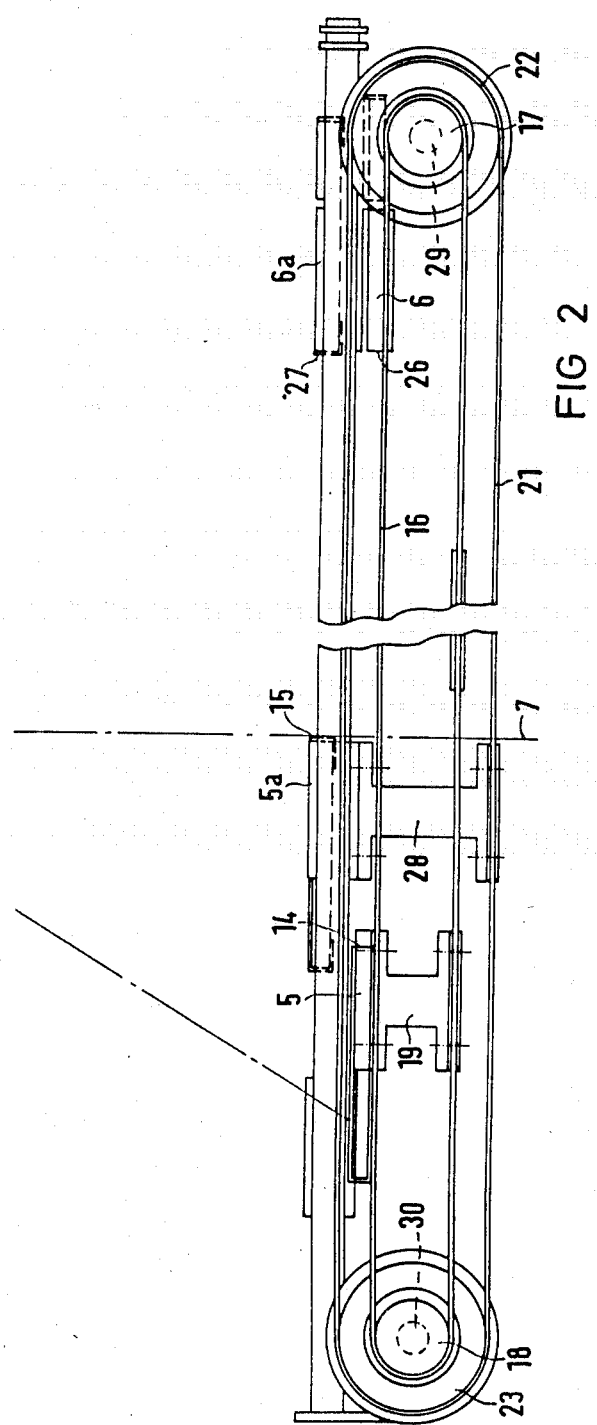

PRIMARY RADIATION DIAPHRAGM FOR X-RAY DIAGNOSTICS DEVICES

BACKGROUND OF THE INVENTION

1. Field of the Invention

The present invention relates to radiation diaphragms for x-ray diagnostics devices, and in particular to a primary radiation diaphragm having at least two pairs of diaphragm plates disposed in different planes and movable oppositely with respect to each other.

2. Description of the Prior Art

Primary radiation diaphragms for x-ray devices are known wherein two pairs of diaphragm plates are movable in opposite directions relative to each other in two parallel planes, so that a rectangular shaping of the x-ray beam is achieved. Adjustment of the pairs of diaphragm plates disposed above each other must be undertaken in a manner such that the opening defining the radiation field is left free.

SUMMARY OF THE INVENTION

It is an object of the present invention to provide a primary radiation diaphragm having two pairs of oppositely movable plates disposed in space parallel planes wherein it is guaranteed that the diaphragm plates cover each other at each diaphragm side in every diaphragm position.

The above object is inventively achieved in a primary radiation diaphragm wherein the diaphragm plates in each pair of diaphragm plates are connected to a belt conducted around a wheel and are thereby adjustable in a plane perpendicular to the direction of propagation of a central ray of the x-ray beam. The wheels to which the pairs of diaphragm plates are respectively connected are of different diameters and are mounted on a common axle, such that the pair of diaphragm plates disposed in a plane closer to the x-ray focus is adjusted by the wheel having a larger diameter, and the pair of diaphragm plates further from the focus is adjusted by the smaller wheel. Thus the plates closer to the x-ray focus move at a faster rate than the plates farther from the focus. At a minimum, two wheels or pulleys having different diameters mounted on a common axle are needed for achieving the different regulating rates of the diaphragm plates in the individual planes.

DESCRIPTION OF THE DRAWINGS

FIG. 2 is a side view of the drive means for the plates in the primary radiation diaphragm shown in FIG. 1.

DESCRIPTION OF THE PREFERRED EMBODIMENTS

Figure 1:
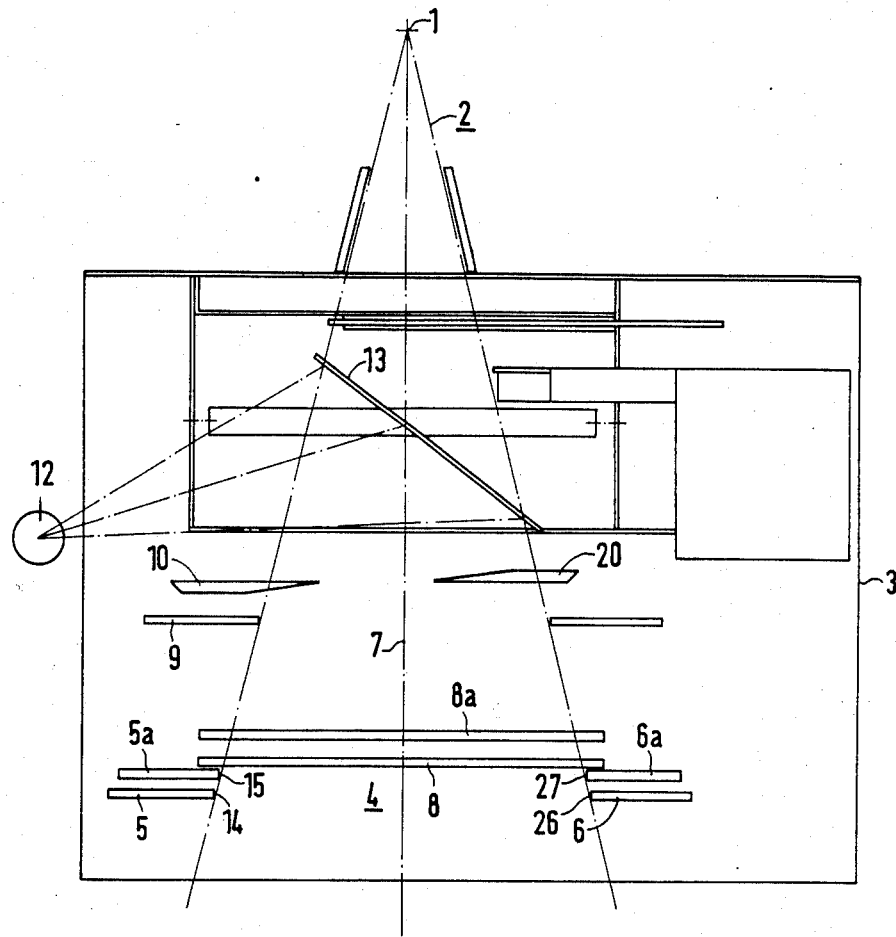
FIG. 1 is a schematic side view of a primary radiation diaphragm constructed in accordance with the principles of the present invention.

A primary radiation diaphragm is generally referenced at 3 in FIG. 1 for use in an x-ray diagnostic system. The system has an x-ray tube with a focus referenced at 1 for generating a fan-shaped x-ray beam which is to be limited by the primary diaphragm 3. The x-ray beam 2 has a central ray 7.

The primary radiation diaphragm 3 includes a rectangular diaphragm 4 comprising a pair of diaphragm plates 5 and 6, disposed in a common plane, and another pair of diaphragm plates 5a and 6a disposed in another common plane parallel to the plane containing the plates 5 and 6. The plates in each pair are movable oppositely relative to each other for thereby defining the width of the x-ray beam 2. Limiting of the x-ray beam 2 in the other direction, that is, the direction perpendicular to the plane of the drawing, is accomplished by two further pairs of diaphragm plates, also disposed in spaced parallel planes, of which only diaphragm plates 8 and 8a can be seen in FIG. 1.

The primary radiation diaphragm 3 also includes an iris diaphragm which covers the corners of the field defined by the rectangular diaphragm 4 with wedge elements, and accordingly adapts the field to be received by the input luminescent screen of an x-ray image intensifier (not shown). A pair of diaphragm plates 10 and 20 is also provided, the plates being in two parallel planes and each having a wedge portion at the side thereof closer to the central beam 7, the wedge portions being partially transparent for the x-radiation. The approach of instruments to the examination subject is thereby visible in the x-ray shadowgraph without diagnostically irrelevant image regions being irradiated. The primary diaphragm 3 further includes a light-beam localizer comprising a light source 12 and a mirror 13, transparent for x-radiation, for making the limited field visible on the examination subject.

The pairs of diaphragm plates 5 and 6, and 5a and 6a, must be adjusted in their respective planes perpendicular to the central ray 7 such that the plates on each diaphragm side overlap at every diaphragm position.

For this purpose, as shown in FIG. 2, the diaphragm plates 5 and 6 are secured to a toothed belt 16 which is conducted around two wheels 17 and 18. In order that the diaphragm plates 5 and 6 will be moved oppositely relative to each other, the diaphragm plate 5 is secured to the lower part of the toothed belt 16 by an adaptor 19, through which the top part of the belt 16 passes unimpeded. The diaphragm plates 5a and 6a are secured to a second toothed belt 21 in an analogous manner, with the plate 5a being secured to the lower portion of the belt 21 by an adaptor 28. The wheels 17 and 22 are mounted on a common axle 29, and the wheels 18 and 23 are mounted on a common axle 30. The wheels 17 and 18 have a smaller diameter than the wheels 22 and 23.

As a consequence of the smaller diameter of the wheels 17 and 18, the diaphragm plates 5 and 6 traverse a smaller distance than the diaphragm plates 5a and 6a given common rotation of the wheels through a specific angle. The diameters of the wheels 17, 18, 22 and 23 are selected with respect to each other such that the regulating or adjustment rate for the diaphragm pair 5a and 6a closer to the focus 1 is greater than the regulating or adjustment rate for the diaphragm plate pair 5 and 6 disposed farther from the focus. Moreover, the diameters are selected such that the parallel diaphragm plates 5 and 5a, and 6 and 6a, on each diaphragm side overlap at every diaphragm position.

An identical means is provided for adjusting the position of the diaphragm plates in the direction perpendicular to the plane of FIGS. 1 and 2, of which, as previously mentioned, only plates 8 and 8a are visible.

In the position of FIG. 2, the parallel diaphragm plates 5 and 5a are shown at a position for the left half of the diaphragm in which the diaphragm is completely closed. The edge 15 of the diaphragm plate 5a, limiting the x-ray beam 2, approaches the central ray 7, whereas the right edge 14 of the diaphragm plate 5 is disposed under the diaphragm plate 5a. Accordingly the diaphragm plates 5 and 5a overlap to such a degree that the diaphragm is completely closed. The diaphragm plates 6 and 6a thereby assume a mirror symmetric position in which the edge 27 of the diaphragm plate 6a is at the central ray 7, and the edge 26 of the diaphragm plate 6 is disposed under the diaphragm plate 6a.

The diaphragm plate 6 and 6a are shown in FIG. 2 in that position in which the diaphragm is commpletely open. The edges 26 and 27 thus are disposed substantially under each other. Due to the selected difference in diameters of the wheels 17 and 22 (and 18 and 23) the regulating rate for the diaphragm plates 5 and 6 is one-half that of the regulating rate for the diaphragm plates 5a and 6a. Because the rate is one-half as large, and the wheels 17 and 22 are rotated for the same amount of time, the regulating distance will assume the same one-half relationship. With the use of two parallel diaphragm plates at each diaphragm side, relatively narrow diaphragm plates can be utilized, thus making the space requirements for the entire diaphragm assembly considerably smaller than conventional devices.

Although modifications and changes may be suggested by those skilled in the art it is the intention of the inventor to embody within the patent warranted hereon all changes and modifications as reasonably and properly come within the scope of his contribution to the art.

I claim as my invention:

1. A primary diaphragm for limiting x-radiation having a central ray emanating from an x-ray focus in an x-ray diagnostic installation, said primary diaphragm comprising:

first and second pairs of diaphragm plates, the plates in each pair being in a common plane and said pairs being in spaced parallel planes perpendicular to said central ray;

a first pair of wheels of a first diameter carried on separate spaced axles;

a second pair of wheels of a second diameter also respectively carried on said spaced axles, said first diameter being smaller than said second diameter;

a first belt entrained around said wheels of said first diameter and having upper and lower portions which move in opposite directions upon rotation of said axles respectively connected to said plates in said first pair of diaphragm plates in a plane farther from said x-ray focus for moving said plates in said first pair toward and away from each other; and a second belt entrained around said wheels of said second diameter and having upper and lower portions which move in opposite directions upon rotation of said axles respectively connected to said plates in said second pair of diaphragm plates in the plane closer to said x-ray focus for moving the plates in said second pair toward and away from each other, said first and second diameters being selected such that said second pair of plates in said plane closer to said focus are moved at a faster rate upon rotation of said axles than the plates in said first pair in the plane farther from said focus and the plates in the spaced planes overlapping at every plate position.

2. A primary diaphragm as claimed in claim 1, wherein said wheels of said second diameter have a diameter which is twice the diameter of said wheels of said first diameter.

* * * * *